United States Patent [19]

Saarinen

[11] Patent Number: 5,491,340
[45] Date of Patent: Feb. 13, 1996

[54] METHOD AND APPARATUS FOR DETERMINATION OF REFINER MECHANICAL PULP PROPERTIES

[75] Inventor: Kari Saarinen, Vaasa, Finland

[73] Assignee: ABB Strömberg Drives OY, Helsinki, Finland

[21] Appl. No.: 256,355

[22] PCT Filed: Jan. 22, 1993

[86] PCT No.: PCT/FI93/00023

§ 371 Date: Jul. 19, 1994

§ 102(e) Date: Jul. 19, 1994

[87] PCT Pub. No.: WO93/15389

PCT Pub. Date: Aug. 5, 1993

[30] Foreign Application Priority Data

Jan. 24, 1992 [FI] Finland .................................. 920341

[51] Int. Cl.⁶ .............................. D21C 7/00; G01N 21/35
[52] U.S. Cl. ........................................ 250/339.06; 162/49
[58] Field of Search ......................... 250/339.06; 162/49

[56] References Cited

U.S. PATENT DOCUMENTS 4,040,743  8/1977  Villaume et al. .
4,514,257  4/1985  Karlsson et al. .
4,743,339  5/1988  Faix et al. ................... 162/49
4,800,279  1/1989  Hieftje et al. .
4,886,576  12/1989  Sloan ......................... 162/49
5,104,485  4/1992  Weyer ........................ 162/49

FOREIGN PATENT DOCUMENTS 0340184    11/1989  European Pat. Off. .
WO82/03688 10/1982  WIPO .
WO84/04594 11/1984  WIPO .
WO86/07458 12/1986  WIPO .
WO87/05109  8/1987  WIPO .

OTHER PUBLICATIONS

Oskar Faix, Hans-Ludwig Schubert and Rudolf Patt, "Continuous Process Control of Pulping by FTIR Spectroscopy." *TAPPI Proceedings—1989 Wood and Pulping Chemistry* pp. 1–8.

Primary Examiner—Constantine Hannaher
Attorney, Agent, or Firm—Birch, Stewart, Kolasch & Birch

[57] ABSTRACT

The invention concerns a method and apparatus for real-time measurement of refiner mechanical pulp quality index such as freeness. According to the method, refiner mechanical pulp transported in a steam-phase carrier is illuminated with electromagnetic radiation, and the change in the radiation spectrum caused by refiner mechanical pulp is detected. According to the method, the change in the radiation spectrum caused by refiner mechanical pulp is measured at a minimum number of four wavelength bands and the measured intensities are computationally processed to obtain the desired index of quality.

3 Claims, 6 Drawing Sheets

CALCULATION RESULTS

| | CSF | | | GROUP VALUES | | |
|---|---|---|---|---|---|---|
| GROUP | LABR. | MODEL | DIF. | GROUP | LABR. | MODEL |
| 1 | 120.00 | 134.06 | -14.06 | | | |
| 2 | 150.00 | 130.41 | 19.59 | | | |
| 3 | 172.00 | 151.41 | 20.59 | | | |
| 4 | 134.00 | 144.03 | -10.03 | | | |
| 5 | 144.00 | 155.73 | -11.73 | | | |
| 6 | 150.00 | 166.96 | -16.96 | | | |
| 7 | 170.00 | 169.85 | 0.15 | | | |
| 8 | 192.00 | 200.62 | -8.62 | | | |
| 9 | 178.00 | 174.66 | 3.34 | | | |
| 10 | 170.00 | 166.80 | 3.20 | | | |
| 11 | 172.00 | 157.44 | 14.56 | | | |
| 12 | 148.00 | 138.71 | 9.29 | | | |
| 13 | 168.00 | 162.08 | 5.92 | | | |
| 14 | 122.00 | 151.09 | -29.09 | | | |
| 15 | 180.00 | 162.21 | 17.79 | | | |
| 16 | 168.00 | 175.62 | -7.62 | | | |
| 17 | 185.00 | 196.88 | -11.88 | | | |
| 18 | 180.00 | 196.15 | -16.15 | | | |
| 19 | 180.00 | 182.90 | -2.90 | | | |
| 20 | 128.00 | 123.80 | 4.20 | | | |
| 21 | 114.00 | 129.71 | -15.71 | | | |
| 22 | 138.00 | 144.51 | -6.51 | | | |
| 23 | 130.00 | 127.53 | 2.47 | | | |
| 24 | 118.00 | 136.93 | -18.93 | | | |
| 25 | 130.00 | 131.46 | -1.46 | | | |
| 26 | 160.00 | 169.09 | -9.09 | | | |
| 27 | 130.00 | 138.90 | -8.90 | | | |
| 28 | 118.00 | 93.78 | 24.22 | | | |
| 29 | 116.00 | 132.23 | -16.23 | | | |
| 30 | 112.00 | 111.21 | 0.79 | | | |
| 31 | 130.00 | 123.71 | 6.29 | | | |
| 32 | 148.00 | 163.27 | -15.27 | | | |
| 33 | 136.00 | 154.67 | -18.67 | | | |
| 34 | 172.00 | 168.10 | 3.90 | | | |
| 35 | 184.00 | 172.15 | 11.85 | | | |
| 36 | 158.00 | 154.61 | 3.39 | | | |
| 37 | 134.00 | 131.33 | 2.67 | | | |
| 38 | 136.00 | 133.24 | 2.76 | | | |
| 39 | 172.00 | 157.03 | 14.97 | | | |
| 40 | 184.00 | 170.46 | 13.54 | | | |
| 41 | 220.00 | 201.56 | 18.44 | | | |
| 42 | 220.00 | 197.96 | 22.04 | | | |
| 43 | 206.00 | 192.16 | 13.84 | | | |

STATISTIC GROUP VALUES

| CORR | PROB | Z | STD | MAX.ERROR | MAX.ERR.INDEX |
|---|---|---|---|---|---|
| 0.89 | 0.00 | 1.40 | 13.21 | -29.09 | 14 |

| 5A |
|---|
| 5B |

CSF

| GROUP | LABR. | MODEL | DIF. | GROUP VALUES | | |
|---|---|---|---|---|---|---|
| | | | | GROUP | LABR. | MODEL |
| 1 | 595.00 | 580.63 | 14.37 | | | |
| 2 | 540.00 | 513.84 | 26.16 | | | |
| 3 | 565.00 | 580.11 | -15.11 | | | |
| 4 | 600.00 | 585.17 | 14.83 | | | |
| 5 | 607.00 | 589.89 | 17.11 | | | |
| 6 | 304.00 | 310.95 | -6.95 | | | |
| 7 | 438.00 | 467.42 | -29.42 | | | |
| 8 | 670.00 | 709.11 | -39.11 | | | |
| 9 | 650.00 | 625.31 | 24.69 | | | |
| 10 | 530.00 | 500.40 | 29.60 | | | |

PRESS RETURN TO CONTINUE

STATISTIC GROUP VALUES

| CORR | PROB | Z | STD | MAX.ERROR | MAX.ERR.INDEX |
|---|---|---|---|---|---|
| 0.97 | 0.00 | 2.17 | 23.58 | -39.11 | 8 |

PRESS RETURN TO CONTINUE

CALCULATION RESULTS

| | TEAR STRENGTH | | | GROUP VALUES | | | |
|---|---|---|---|---|---|---|---|
| GROUP | LABR. | MODEL | DIF. | GROUP | LABR. | MODEL | DIF. |
| 1 | 8.90 | 9.42 | -0.52 | | | | |
| 2 | 9.30 | 9.59 | -0.29 | | | | |
| 3 | 9.60 | 9.79 | -0.19 | | | | |
| 4 | 9.60 | 9.96 | -0.36 | | | | |
| 5 | 10.30 | 10.02 | 0.28 | | | | |
| 6 | 10.40 | 10.25 | 0.15 | | | | |
| 7 | 10.20 | 10.01 | 0.19 | | | | |
| 8 | 9.90 | 9.89 | 0.01 | | | | |
| 9 | 9.60 | 9.78 | -0.18 | | | | |
| 10 | 9.20 | 9.49 | -0.29 | | | | |
| 11 | 10.10 | 9.83 | 0.27 | | | | |
| 12 | 9.90 | 10.00 | -0.10 | | | | |
| 13 | 10.00 | 10.08 | -0.08 | | | | |
| 14 | 9.90 | 10.11 | -0.21 | | | | |
| 15 | 10.00 | 10.08 | -0.08 | | | | |
| 16 | 9.70 | 10.01 | -0.31 | | | | |
| 17 | 9.40 | 9.25 | 0.15 | | | | |
| 18 | 8.90 | 9.34 | -0.44 | | | | |
| 19 | 9.10 | 9.55 | -0.45 | | | | |
| 20 | 10.00 | 10.00 | -0.00 | | | | |
| 21 | 9.80 | 9.43 | 0.37 | | | | |
| 22 | 8.90 | 8.70 | 0.20 | | | | |
| 23 | 9.10 | 9.34 | -0.24 | | | | |
| 24 | 9.10 | 8.89 | 0.21 | | | | |
| 25 | 9.70 | 9.15 | 0.55 | | | | |
| 26 | 9.40 | 9.31 | 0.09 | | | | |
| 27 | 9.40 | 9.31 | 0.09 | | | | |
| 28 | 9.90 | 9.79 | 0.11 | | | | |
| 29 | 10.00 | 10.02 | -0.02 | | | | |
| 30 | 10.60 | 10.25 | 0.35 | | | | |
| 31 | 10.00 | 10.14 | -0.14 | | | | |
| 32 | 10.60 | 10.12 | 0.48 | | | | |
| 33 | 10.50 | 10.10 | 0.40 | | | | |

STATISTIC GROUP VALUES

| CORR | PROB | Z | STD | MAX.ERROR | MAX.ERR.INDEX |
|---|---|---|---|---|---|
| 0.82 | 0.00 | 1.15 | 0.28 | 0.55 | 25 |

FIG. 6

METHOD AND APPARATUS FOR DETERMINATION OF REFINER MECHANICAL PULP PROPERTIES

BACKGROUND OF THE INVENTION

1. Field of the Invention

The present invention concerns on-line measurement of refiner mechanical pulp quality indices such as freeness, specific surface, fiber distribution, tear strength or average fiber length.

More specifically, the invention concerns a method according to the characterizing part of claim 1 for determination of refiner mechanical pulp properties.

Furthermore, the invention concerns an apparatus for determination of refiner mechanical pulp quality indices.

DESCRIPTION OF BACKGROUND ART

Conventionally, refiner mechanical pulp quality is characterized by different kinds of pulp strength indices, freeness and optical properties.

Forgacs investigated the strength properties and particle size distributions of refiner mechanical pulp in 1962. The outcome of his investigations was that the properties of a refiner mechanical pulp web such as burst strength, tear strength, bulk and wet web tensile strength could be predicted for a wide range of SGW pulps on the basis of only two pulp characterization indices:

1. Length factor (in short, L factor), which is characteristic of the fiber length distribution.

2. Form factor, which is characteristic of the degree of fiber surface fibrillation. Forgacs characterized this factor as specific surface (also called the S factor) of the +100 mesh fraction obtained using the Bauer-McNett classifier.

Later analyses on the results obtained by Forgacs and others have shown that the following equation is valid over a very wide range of pulp production methods and different wood grades:

$$A_L = 0.6 + K/L^2,$$

where $A_L$=specific surface (m²/g) of a fiber fraction with a weighted average fiber length L K=K factor, an index characteristic of the degree of fiber surface fibrillation (essentially equal to the Forgacs' S. factor).

The Canadian Standard Freeness (CSF) test is basically a measurement of the fiber specific surface. According to the literature, the following logarithmic relationship exists between the fiber specific surface and CSF:

$$A_{TOT} = -3.03 ln(CSF) + 21.3$$

where $A_{TOT}$=total specific surface of refiner mechanical pulp (m²/g).

Conventional Freeness Testers and Their Operating Principles

Freeness can be measured from pulp taken from the latency chest 2 which is in line immediately next to the stage II refiner 1 in the system illustrated in FIG. 1. Some testers incorporate a built-in latency elimination, thus requiring no separate latency chest. Such testers as well need some kind of intermediate container in which pulp consistency is essentially lower than in the pulp immediately discharged from the refiner. With the help of a steam-phase carrier, the pulp is transferred from the refiner along a blow pipe 3 further in the process.

Conventional, almost on-stream measuring freeness testers can be divided into two categories on the basis of their operating principle: filtration and permeability testers.

Filtration Testers

Filtration is defined by the following equation:

$$\frac{dV}{dt} = \frac{A_s^2 \times dP}{\mu \times c \times V \times R}$$

where V=flow volume
$A_S$=screen cross-flow area
dP=differential pressure over pulp bed
µ=viscosity coefficient
c=consistency
R=average filtration resistance imposed by fibers.

Assuming P to be constant and taking into account the physical dimensions and boundary conditions of the tester, the filtration time of the tester can be solved:

$$dt = t_2 - t_1 = \frac{\mu \times c \times R \times (V_2^2 - V_1^2)}{2 \times A_s^2 \times dP}$$

where R=average specific filtration resistance of the pulp
$V_1$=measurement chamber volume from screen to lower electrode
$V_2$=measurement chamber volume from screen to upper electrode
$t_1$=filtration time to volume $V_1$
$t_2$=filtration time to volume $V_2$
dt=filtration time measured by the tester With the tester operating at constant temperature and consistency, the filtration time has a linear relationship with the specific filtration resistance R:

$$dt = \sigma * R$$

The value of R is affected by the specific surface and volume of the fibers. At high freeness values, the correlation between R and CSF is good, but at lower freeness values (50 ... 100 ml) a significant loss of sensitivity is encountered.

Permeability Testers

These testers are based on the Darcy's law:

$$U = \frac{K \times dP}{\mu \times L}$$

where K=permeability
dP=differential pressure over the fiber bed
µ=viscosity coefficient
L=fiber bed thickness
U=flow velocity through the fiber bed.

The permeability of the fiber bed can be obtained from the Kozeny-Carman equation:

$$K = \frac{\epsilon^3 \times K}{5.55 \times S_0^2 \times (1 - \epsilon)^2}$$

where $S_o$=specific surface of the fibers
$\epsilon$=porosity.

When the pressure P is maintained constant in the measurement chamber, the flow velocity U is closely related to changes in the degree of fiberization of the fiber surface. Consequently, the flow velocity is a function of the CSF value.

Fiber Length Analyzers

FIGS. 2 and 3 illustrate conventional, almost on-stream operating fiber length analyzers are based on the sampling of the pulp flow and subsequent analysis of the highly diluted sample with the help of a detector 12 which measures the length of the shadow cast by a single fiber illuminated with a source 10 of light. In such a PQM analyzer the sampling and analysis functions are fully automatic. The sample is taken after the latency chest. The PQM analyzer illustrated in FIG. 3 also measures the thickness of the fiber. The rays emitted from sources of light are in this embodiment aligned perpendicular to the center axes of the detectors.

The FS-200 analyzer manufactured by Kajaani Automation is based on manual sampling. The analysis is fully automatic.

However, a number of drawbacks remain. Measurement results immediately after the first refiner cannot be obtained. So, changes occurring at the refiners cannot be noticed in the analyzer output until 30 . . . 60 minutes later as the measurement is taken after the latency chest. The measurements are discontinuous at certain intervals due to the sampling principle employed.

SUMMARY AND OBJECTS OF THE INVENTION

It is an object of the present invention to overcome the drawbacks of the above described technology and to achieve an entirely novel method and apparatus for determining pulp quality by virtue of performing a direct analysis of the physical properties of the fiber and predicting the conventional fiber characterizing indices on the basis thereof.

The invention is based on illuminating the refiner mechanical pulp with electromagnetic radiation in the wavelength range 0.1 . . . 10 μm already in the blow transfer pipe leaving the refiner and then measuring either the component reflected from or transmined through the refiner mechanical pulp simultaneously at a minimum number of four different wavelength bands and computing the desired quality index from thus obtained intensity values, advantageously using the principal component method.

The magnitude of reflected intensity is dependent on, i.e., the specific surface, fiber lengths and number of fiber particles present. Furthermore, particles of different sizes reflect the radiation in a different manner. Computational combinations of the spectral intensities give new variables, for which the principal component method can be applied to compute linear calibration coefficients for each desired quality index.

The new variables must be found such that they have orthogonally characteristic of the specific surface, fiber length, fiber distribution, refiner mechanical pulp consistency and other possible quality indices of the refiner mechanical pulp.

During calibration, only one of properties to be measured is changed at a time. The computation method employed in calibration compensates for the variations in the measured spectrum caused by other variables except those related to the desired measurement variable, e.g., the consistency.

More specifically, the method according to the invention is characterized by simultaneously measuring the change in the spectrum of the radiation caused by the refiner mechanical pulp at a minimum number of four different wavelength bands and processing the measured radiation intensity values by computational methods to obtain the freeness value.

Furthermore, the apparatus according to the invention is characterized by the measurement elements provided with means for simultaneous measurements at a minimum number of four wavelength bands.

The invention offers significant benefits.

The method and apparatus according the present invention achieves undelayed detection of changes in pulp quality, whereby immediate corrective measures can as well be applied. Consequently, separate sampling and/or dilution of the pulp is unnecessary. The direct measurement also offers an improved modelling of the refiner control, because the error caused by measurement delay can be neglected in such a model.

BRIEF DESCRIPTION OF THE DRAWINGS

The invention is next examined in greater detail with the help exemplifying embodiments illustrated in the attached drawing, in which

FIGS. 5A and 5B show computational results in tabular form for freeness obtained by virtue of the method according to the invention.

FIG. 6 shows computational results in tabular form for tear strength obtained by virtue of the method according to the invention.

DETAILED DESCRIPTION OF THE PREFERRED EMBODIMENTS

Figure 1:
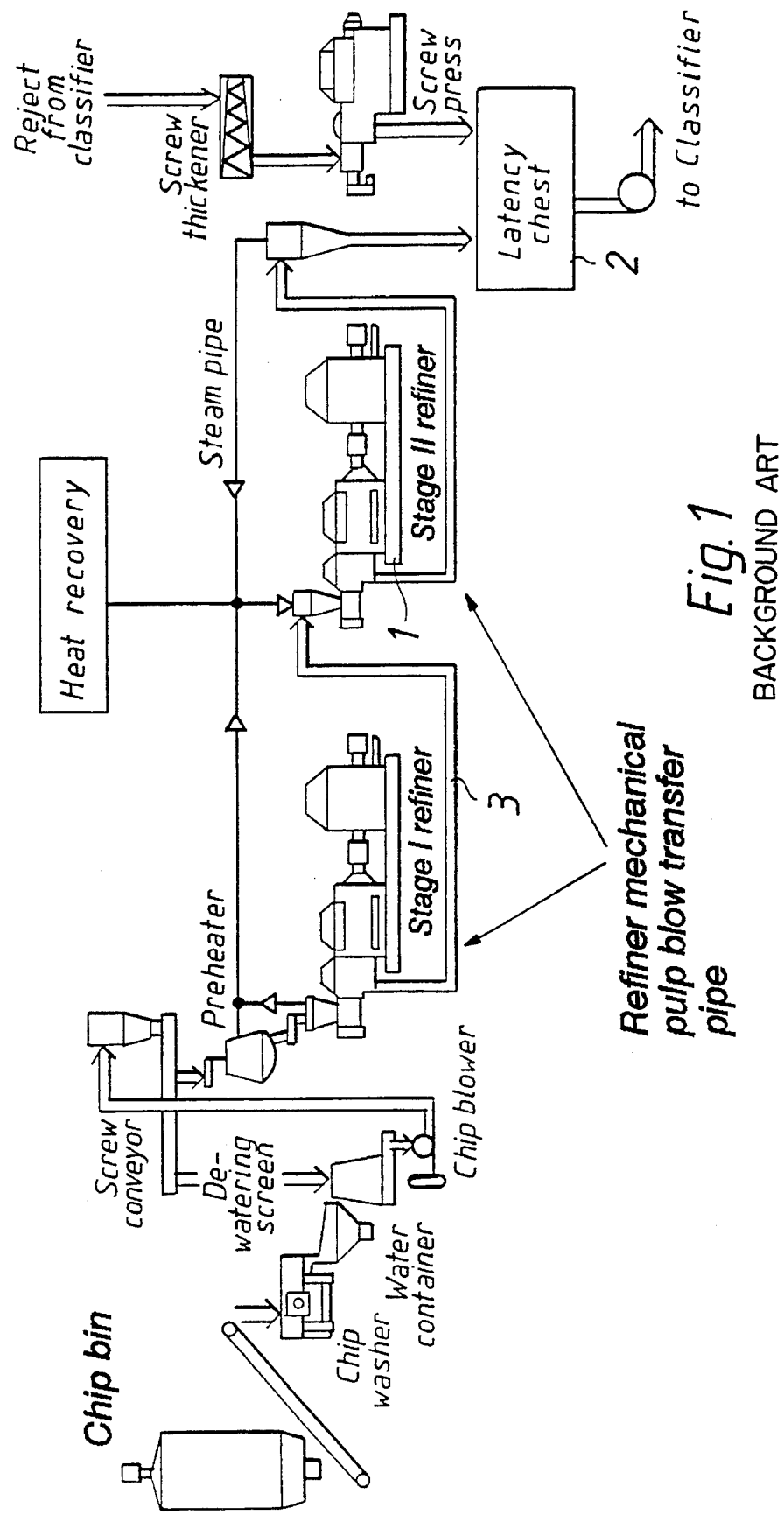
FIG. 1 shows diagrammatically the process environment to which the invention is applied.
Figure 2:
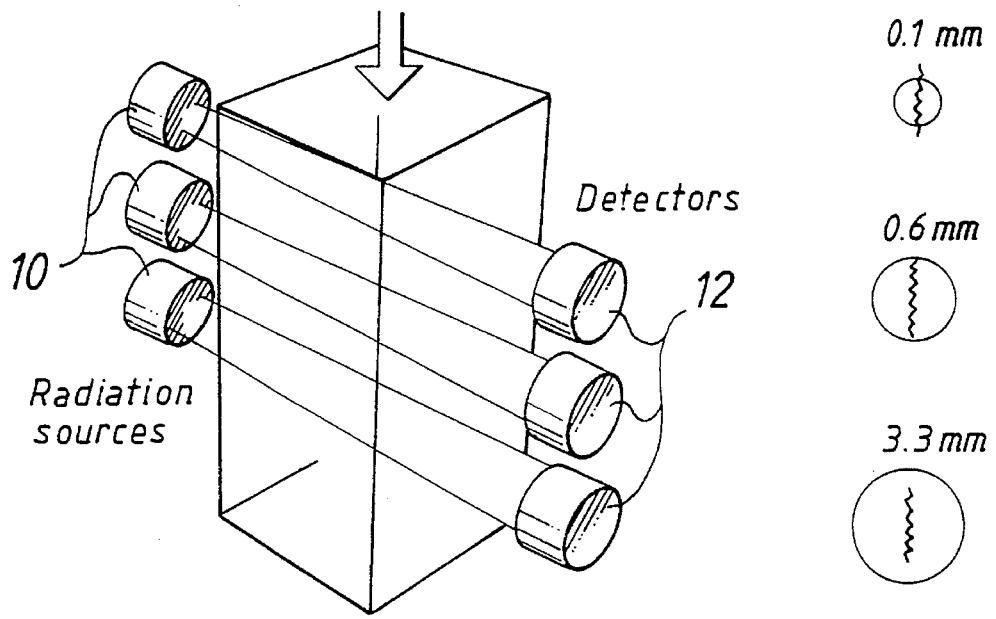
FIG. 2 shows a perspective view of a prior-art fiber length analyzer.
Figure 3:
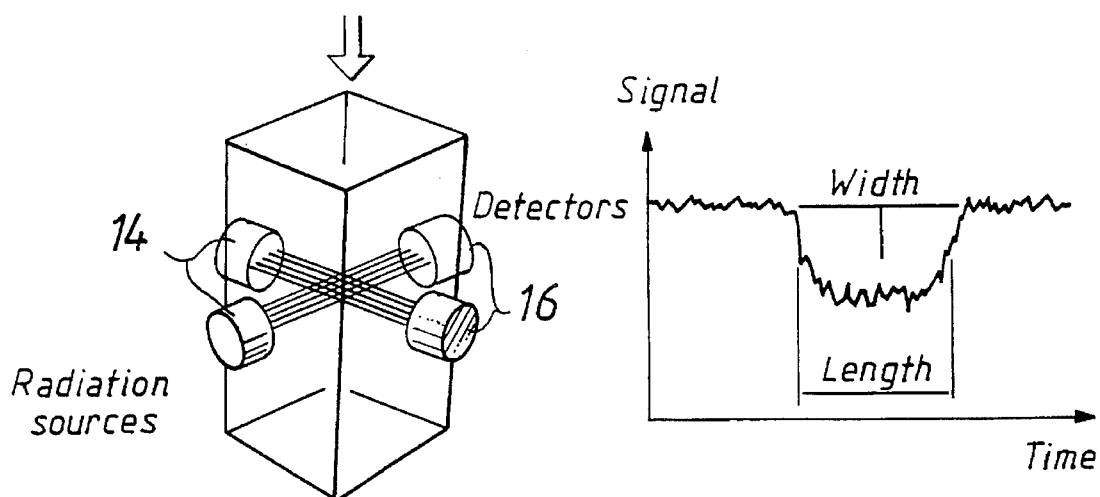
FIG. 3 shows a perspective view of another prior-art fiber length analyzer.

FIGS. 1 . . . 3 are evident on the basis of the descriptions given in the general part of the foregoing text.

Figure 4:
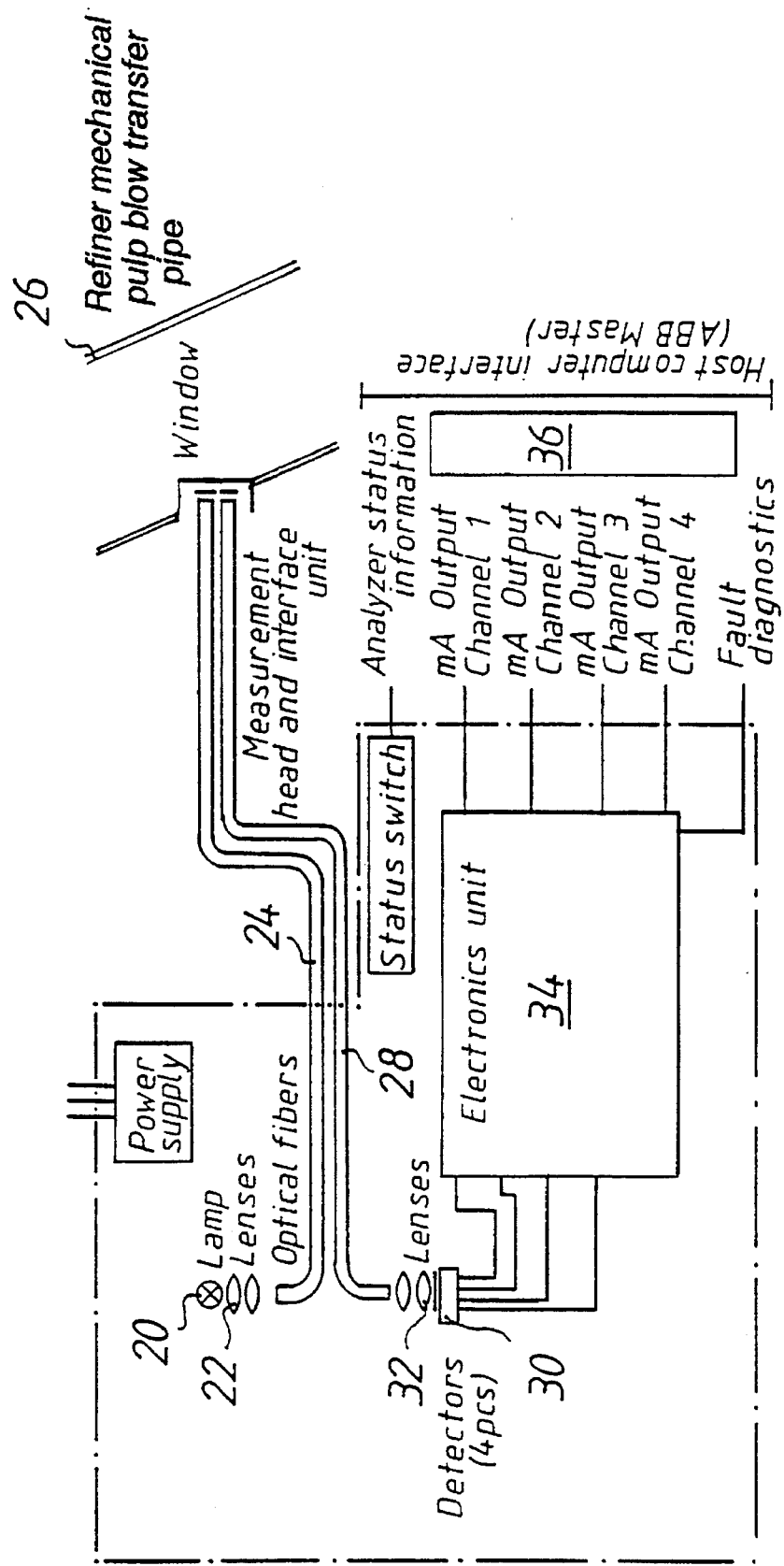
FIG. 4 shows a perspective view of an apparatus suited to implement the method according to the invention.

FIG. 4 illustrates the construction of the analyzer which basically is similar to that of a high-consistency analyzer. The IR-range source of radiation is a halogen lamp 20, whose intensity is controlled with a high precision. The emitted radiation is focused onto the input ends of optical fibers by means of mirrors and lenses 22. The radiation is then transmitted along the optical fibers 24 into a process pipe 26. The process pipe 26 corresponds to the blow pipe 3 of the diagram in FIG. 1. The radiation reflected from the pulp is collected with another optical fiber 28 and routed to detectors 30. The detectors 30 are preceded by grids 32 which transmit only the desired wavelength bands from the radiation. The intensity signal for each wavelength band is amplified by a parallel amplifier array, that is, each band has a dedicated amplifier 34. Calculation is implemented with a computing unit 36.

The measurement is appropriately performed using a wavelength range of 0.1 . . . 10 μm.

The amplified signals and combinations thereof are processed by computational methods to obtain new variables for which the correction coefficients are computed during calibration.

The calibration coefficients are computed using the principal component method. The principal component method is described in, e.g., textbooks by Martens, Naes; Multivariable calibration; Wiley-Interscience 89 (pp. 97 . . . 101) and C. R. Rao; Linear Statistical Inference and its Application (pp. 590 . . . 593); Wiley-Interscience 65.

The aim of the principal component method is to express the information embedded in the variables (measurement results) with a reduced number of variables, called the principal components.

Example

Freeness Measurement

Four measurement wavelengths are employed:

$I_1=1.450$ μm
$I_2=1.700$ μm
$I_3=1.960$ μm
$I_4=2.100$ μm

The measurement results are computationally processed to form new variables (6 pcs.):

$x_1=\ln(I_2/I_3)$, $x_2=\ln(I_1/I_4)$, $x_3=\ln(I_2/I_4)$
$x_4=\ln(I_1/I_3)$, $x_5=\ln(I_3/I_4)$, $x_6=\ln(I_1/I_2)$

These are written in the form of a calibration equation with the help of the principal component method:

Calibration equation:

$$CSF = a_1 x_1 + a_2 x_2 + a_3 x_3 + a_4 x_4 + a_5 x_5 + a_6 x_6 + a_0$$

The calibration coefficients are dependent on the measurement site and variation range of freeness. In the example the coefficients were obtained using three principal components.

The following results were obtained over the freeness range of 300 . . . 600 ml (FIG. 5):
corr 0.97 standard error (std) 23 ml ≈ 4% of test mean The following results were obtained over the freeness range of 110 . . . 220 ml (FIG. 5):
corr 0.89 standard error (std) 13 ml ≈ 8% of test mean FIG. 6 shows the corresponding modelling related to tear strength.

Mathematic Application of the Principal Component Method

The number of test points used in calibration is denoted k. For each test point i, the intensity of reflected radiation $I_{i1}$, $I_{i2}$, $I_{i3}$ and $I_{i4}$ is measured at four wavelengths and the freeness $u_i$ (CSF) corresponding to each measurement is determined using laboratory analysis methods.

1. New variables $x_{ij}$ (i=1 . . . k, j=1 . . . 6) are computed, e.g. $x_{i1}=\ln(I_{i2}/I_{i3})$ and formed into a matrix $X^{k \times 6}$.

$$X = \begin{bmatrix} x_{11} & x_{12} & \cdots & x_{16} \\ x_{21} & x_{22} & \cdots & x_{26} \\ \vdots & \vdots & & \vdots \\ x_{k1} & x_{k2} & \cdots & x_{k6} \end{bmatrix} \begin{matrix} \text{Testpoint1} \\ \text{Testpoint2} \\ \\ \\ \text{Testpoint}k \end{matrix} \quad (1)$$

2. A covariance matrix $A^{6 \times 6}$, which is a symmetric square matrix, is computed.

$$A = X^T X = \begin{bmatrix} \sum_{i=1}^{k} x_{i1}x_{i1} & \sum_{i=1}^{k} x_{i1}x_{i2} & \cdots & \sum_{i=1}^{k} x_{i1}x_{i6} \\ \sum_{i=1}^{k} x_{i2}x_{i1} & \sum_{i=1}^{k} x_{i2}x_{i2} & \cdots & \sum_{i=1}^{k} x_{i2}x_{i6} \\ \vdots & \vdots & & \vdots \\ \sum_{i=1}^{k} x_{i6}x_{i1} & \sum_{i=1}^{k} x_{i6}x_{i2} & \cdots & \sum_{i=1}^{k} x_{i6}x_{i6} \end{bmatrix} \quad (2)$$

3. The eigenvalues and eigenvectors of the matrix A are computed. The matrix $A^{N \times N}$ is said to have an eigenvector $v_i$ and eigenvalue $\lambda_i$ if $$A v_i = \lambda_i v_i \quad (3)$$

A symmetric positive-definite NxN matrix has N different eigenvalues. If A is symmetric, the eigenvalues are generally solved in two phases. The matrix A is first written in tridiagonal form with the help of the Householder transform. Next, the OR algorithm is used to solve the eigenvalues and eigenvectors of the tridiagonal matrix.

This phase is described in greater detail in, e.g., the publication:

Smith, B. T. et al, Matrix Eigensystem Routines - EISPACK Guide, 2nd Ed., Vol. 6 of Lecture Notes in Computer Science, New York, Springer-Verlag (1976).

The eigenvalues are written in the matrix $U^{6 \times 6}$ so that the eigenvector corresponding to the largest eigenvalue is placed in first column, the eigenvector corresponding to the second largest eigenvalue in the second column, etc.

4. The principal component matrix $P^{k \times 6}$ is computed as the product of the matrices X and U:

$$P = X U \quad (4)$$

5. For the desired number of principal components, in the example for the three first principal components, the calibration coefficients $b_j$ (j=1, 2, 3) are computed using the method of least-squares for a single variable. The coefficients $b_j$ can be computed one at a time, since the principal components are orthogonal to each other. In other words, the minimum of the sum of squares is computed $$\min_{b_j \in \mathbb{R}} \sum_{i=1}^{k} (y_i - b_j P_{ij})^2, j = 1, 2, 3 \quad (5)$$

to obtain the coefficients $b_1$, $b_2$ and $b_3$. The corresponding calibration method is $$CSF_i = b_1 P_{i1} + b_2 P_{i2} + b_3 P_{i3} \quad (6)$$

6. The coefficients $a_i$ (i=1, . . . 6) are computed as follows:
$P_{ij}$ in Equation (6) is substituted by the corresponding value computed from Equation (4):

$$\begin{aligned} CSF_i = & b_1(U_{11}X_{i1} + U_{21}X_{i2} + \ldots + U_{61}X_{i6}) + \\ & b_2(U_{12}X_{i1} + U_{22}X_{i2} + \ldots + U_{62}X_{i6}) + \\ & b_3(U_{13}X_{i1} + U_{23}X_{i2} + \ldots + U_{63}X_{i6}) \end{aligned}$$

The coefficients of the terms $X_{ij}$ are combined to obtain the coefficients $a_i$:

$$a_1 = (b_1U_{11} + b_2U_{12} + b_3U_{13})$$
$$a_2 = (b_1U_{21} + b_2U_{22} + b_3U_{23})$$
$$\vdots$$
$$a_6 = (b_1U_{61} + b_2U_{62} + b_3U_{63})$$

The number of the principal components used in calibration is determined by the desired computational accuracy. It must be noted that a greater number of the principal components increases the computing effort and simultaneously requires more computational capacity and/or lengthens the computing time.

The method is also applicable to the measurement of specific surface, fiber length, fiber distribution or tear strength.

The point of measurement can be situated in either the blow pipe leaving stage I refiner or the blow pipe leaving stage II refiner.

In lieu of four or more wavelength bands, a certain wavelength band can be covered by a continuous sweep, whereby the number of wavelength bands in the sense of the definitions according to the invention becomes infinite. In digital equipment embodiments, however, such a sweeping arrangement is implemented by measurement over a discrete number of wavelengths.

I claim:

1. A method for on-stream measurement of a refiner mechanical pulp freeness comprising the following steps:

illuminating refiner mechanical pulp transported in a steam-phase carrier by electromagnetic radiation in the wavelength range of 0.1 . . . 10 µm;

measuring the change in the radiation caused by the refiner mechanical pulp;

characterized in that:

simultaneously measuring the change in the spectrum of the radiation caused by the refiner mechanical pulp at a minimum number of four different wavelength bands; and processing the measured radiation intensity values by computational methods to obtain the freeness value.

2. The measurement method as defined in claim 1, characterized in that, for the calibration of the measurement system, the freeness is measured multiple times simultaneously with the intensity measurements, the measurement results are processed into new variables, and the dependence of freeness on the new variables is determined computationally using the principal component method.

3. An apparatus for on-line measurement of a refiner mechanical pulp freeness, said apparatus comprising:

radiation source elements for illuminating refiner mechanical pulp transported in a steam-phase carrier by electromagnetic radiation, measurement elements for detecting the change in the spectrum of the radiation caused by the refiner mechanical pulp, at least one optical fiber for routing the radiation reflected by or transmitted through the refiner mechanical pulp to said measurement elements, and computing elements for processing the measured intensity data into information on freenes, characterized in that the measurement elements are provided with means for simultaneous measurements at a minimum number of four wavelength bands.

* * * * *